US008921632B2

(12) United States Patent
Montalbano et al.

(10) Patent No.: US 8,921,632 B2
(45) Date of Patent: *Dec. 30, 2014

(54) PRODUCING 1-BUTENE FROM AN OXYGENATE-TO-OLEFIN REACTION SYSTEM

(75) Inventors: Joseph A. Montalbano, Bartlett, IL (US); Steven Lee Krupa, Fox River Grove, IL (US); John Joseph Senetar, Naperville, IL (US); Joseph H. Gregor, Itasca, IL (US); Andrea G. Bozzano, Northbrook, IL (US); Gary S. Sandhu, Hanover Park, IL (US)

(73) Assignee: UOP LLC, Des Plaines, IL (US)

( * ) Notice: Subject to any disclaimer, the term of this patent is extended or adjusted under 35 U.S.C. 154(b) by 374 days.

This patent is subject to a terminal disclaimer.

(21) Appl. No.: 13/193,780

(22) Filed: Jul. 29, 2011

(65) Prior Publication Data
US 2012/0041244 A1    Feb. 16, 2012

Related U.S. Application Data

(60) Provisional application No. 61/372,238, filed on Aug. 10, 2010.

(51) Int. Cl.
| | | |
|---|---|---|
| C07C 2/00 | (2006.01) | |
| C07C 41/06 | (2006.01) | |
| C07C 1/20 | (2006.01) | |
| C07C 4/02 | (2006.01) | |
| C07C 4/04 | (2006.01) | |
| C07C 5/03 | (2006.01) | |
| C07C 11/04 | (2006.01) | |
| C07C 11/06 | (2006.01) | |
| C07C 11/08 | (2006.01) | |

(52) U.S. Cl.
CPC . *C07C 41/06* (2013.01); *C07C 1/20* (2013.01); *C07C 4/02* (2013.01); *C07C 4/04* (2013.01); *C07C 5/03* (2013.01); *C07C 11/04* (2013.01); *C07C 11/06* (2013.01); *C07C 11/08* (2013.01)
USPC ........... 585/300; 585/639; 585/641; 585/302; 585/303; 585/650; 585/651; 585/652; 585/653

(58) Field of Classification Search
USPC ......... 585/300, 304, 301, 302, 303, 639, 643, 585/641, 642
See application file for complete search history.

(56) References Cited

U.S. PATENT DOCUMENTS

| | | | | |
|---|---|---|---|---|
| 4,423,264 A * | 12/1983 | Juguin et al. | ................... | 585/255 |
| 6,005,150 A | 12/1999 | Vora | | |
| 6,049,017 A * | 4/2000 | Vora et al. | ...................... | 585/324 |
| 2005/0150817 A1 * | 7/2005 | Tallman et al. | ................ | 585/648 |
| 2008/0154078 A1 * | 6/2008 | Bozzano et al. | ............. | 585/324 |
| 2011/0137095 A1 * | 6/2011 | Chewter et al. | ................ | 585/323 |

* cited by examiner

*Primary Examiner* — In Suk Bullock
*Assistant Examiner* — Sharon Pregler
(74) *Attorney, Agent, or Firm* — Arthur E Gooding

(57) ABSTRACT

1-butene is recovered as a purified product from an MTO synthesis and especially from an integrated MTO synthesis and hydrocarbon pyrolysis system in which the MTO system and its complementary olefin cracking reactor are combined with a hydrocarbon pyrolysis reactor in a way that facilitates the flexible production and recovery of olefins and other petrochemical products, particularly butene-1 and MTBE.

20 Claims, 4 Drawing Sheets

PRODUCING 1-BUTENE FROM AN OXYGENATE-TO-OLEFIN REACTION SYSTEM

CROSS-REFERENCE TO RELATED APPLICATION

This application claims the benefit of U.S. Provisional Application No. 61/372,238 filed Aug. 10, 2010.

FIELD OF THE INVENTION

The present invention broadly relates to a process resulting from an integration of an oxygenate to olefin conversion system with a hydrocarbon pyrolysis system. The process is designed to efficiently produce light olefins, i.e., ethylene and propylene, as well as other commercially important products from disparate feed sources.

BACKGROUND OF THE INVENTION

Ethylene and propylene (light olefins) are commercially important chemicals. Ethylene and propylene are useful in a variety of processes for making plastics and other chemical compounds.

The prior art is always looking for more efficient ways to produce greater yields of light olefins, and especially propylene, from hydrocarbon feed materials.

One important source of light olefins is based on the pyrolysis, e.g., the steam and catalytic cracking, of selected petroleum feed materials. These procedures also produce significant quantities of other hydrocarbon products.

Another, more recent source of light olefins is the oxygenate to olefins conversion process and specifically the methanol-to-olefins (MTO) process.

The MTO process is more effective in producing light olefins than conventional hydrocarbon pyrolysis systems.

Instead of using a hydrocarbon source, this process is based on converting an oxygenate, such as methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof, and preferably methanol to olefins in the presence of a molecular sieve catalyst.

Presumably, the disparate nature of the feed materials utilized in these two sources of light olefins, as well as the compositional differences in the respective reaction products discharged from these separate processes have prevented the prior art from considering the advantages of integrating these separate syntheses.

The present invention focuses on an improved light olefins synthesis process created by a judicious integration of an oxygenate to olefin conversion system (MTO) with a hydrocarbon pyrolysis system.

SUMMARY OF THE INVENTION

In one embodiment, the present invention provides a light olefins synthesis process comprising:
(a) passing an oxygenate feed to an oxygenate to olefin reactor to contact the oxygenate feed with a molecular sieve catalyst and to convert oxygenate to light olefins which are discharged from the oxygenate to olefin reactor in an effluent stream;
(b) separating the effluent stream into a first light olefins stream separate from a first stream containing C4 and higher hydrocarbons;
(c) selectively hydrogenating and then cracking the first stream containing C4 and higher hydrocarbons to form a first cracked gas effluent stream containing light olefins;
(d) separately cracking a hydrocarbon stream to form a second cracked gas effluent stream containing light olefins;
(e) co-fractionating the first and second cracked gas effluent streams to produce a second light olefins stream separate from a second stream containing C4 and higher hydrocarbons;
(f) co-conditioning the first and second light olefins streams to remove acid gases and produce a conditioned steam; and
(g) separating the conditioned stream into an ethylene product stream, a propylene product stream and a stream containing C4 hydrocarbons.

In another embodiment, the present invention provides a light olefins synthesis process comprising:
(a) passing an oxygenate feed to an oxygenate-to-olefin reactor to contact the oxygenate feed with a molecular sieve catalyst and to convert oxygenate feed to light olefins which are discharged from the oxygenate-to-olefin reactor in an effluent stream;
(b) separating the effluent stream into a first light olefins stream separate from a first stream containing C4 and higher hydrocarbons;
(c) selectively hydrogenating and then cracking the first stream containing C4 and higher hydrocarbons to form a first cracked gas effluent stream containing light olefins;
(d) separately cracking a hydrocarbon stream to form a second cracked gas effluent stream containing light olefins, wherein the second cracked gas effluent stream containing light olefins comprises a stream containing C8 and lighter hydrocarbons produced as an overhead of a water quench;
(e) removing C6 and heavier hydrocarbons from the stream of C8 and lighter hydrocarbons by compression;
(f) co-fractionating the first cracked gas effluent stream and the second cracked gas effluent stream from which C6 and heavier hydrocarbons have been removed to produce a second light olefins-containing stream separate from a second stream containing C4 and higher hydrocarbons;
(g) co-conditioning the first and second light olefins-containing streams to remove acid gases and produce a conditioned stream; and
(h) separating the conditioned stream into an ethylene product stream, a propylene product stream and a stream containing C4 hydrocarbons.

In another embodiment, the present invention provides a light olefins synthesis process wherein the separate cracking of a hydrocarbon stream in step (d) is accomplished by steam pyrolysis of a feed comprising one or more of naphtha, liquefied petroleum gas (LPG), propane, ethane, raffinate, gas condensates, atmospheric gas oils and hydrocracker bottoms.

In another embodiment, at least a portion of the stream containing C4 hydrocarbons separated from the conditioned stream in step (g) or (h) is recycled to be cracked with the first stream containing C4 and higher hydrocarbons.

In another embodiment, one portion of the second stream containing C4 and higher hydrocarbons is optionally selectively hydrogenated and then cracked with the first stream containing C4 and higher hydrocarbons and optionally another portion of the second stream containing C4 and higher hydrocarbons is cracked with the hydrocarbon stream.

In another embodiment, the separate cracking of the hydrocarbon stream of step (d) forms the second cracked gas effluent stream containing light olefins and a separate pyrolysis gasoline stream (alternatively referred to a pyrolysis gas and pygas) containing C4 and higher hydrocarbons.

In still another embodiment, the pyrolysis gas stream containing C4 and higher hydrocarbons is selectively hydrogenated to produce a third stream containing C4 and higher hydrocarbons, and at least a portion of the third stream containing C4 and higher hydrocarbons is cracked with the first stream containing C4 and higher hydrocarbons.

In an alternative embodiment, at least a portion of the pyrolysis gas stream containing C4 and higher hydrocarbons is blended with the first and second cracked gas effluent streams containing light olefins to produce a blended stream prior to the co-fractionation of step (e).

In yet another embodiment, the co-fractionation of step (e) or (f) comprises separating the first and second cracked gas effluent streams containing light olefins into a first stream containing C5 and lighter hydrocarbons and a first stream containing C5 and higher hydrocarbons.

In still another embodiment, the first stream containing C5 and lighter hydrocarbons is treated to separate the second light olefins-containing stream from the second stream containing C4 and higher hydrocarbons.

In another embodiment, the co-fractionation of the blended stream of the pyrolysis gas stream containing C4 and higher hydrocarbons and the first and second cracked gas effluent streams containing light olefins produces the first stream containing C5 and lighter hydrocarbons and the first stream containing C5 and higher hydrocarbons.

In another embodiment, the first stream containing C5 and higher hydrocarbons is treated to separate a stream containing C6 and higher hydrocarbons from a second stream containing C4 hydrocarbons In still another embodiment, at least a portion of the second stream containing C4 hydrocarbons is selectively hydrogenated and cracked with the first stream containing C4 and higher hydrocarbons.

In yet another embodiment, the co-fractionation of step (f) comprises separating the first and second cracked gas effluent streams containing light olefins into a first stream containing C5 and lighter hydrocarbons and a pygas stream containing C5 and higher hydrocarbons.

In still another embodiment, the at least a portion of first stream containing C5 and lighter hydrocarbons is treated to separate the second light olefins-containing stream from the second stream containing C4 and higher hydrocarbons.

In another embodiment, at least a portion of the pygas stream containing C5 and higher hydrocarbons is hydrogenated and then separated into a stream containing C6 and higher hydrocarbons and a stream containing C5 and lighter hydrocarbons In still another embodiment, at least a portion of the stream containing the C5 and lighter hydrocarbons separated from the pygas stream is optionally selectively hydrogenated and then cracked with the first stream containing C4 and higher hydrocarbons.

In another embodiment, at least a portion of the pygas stream containing C5 and higher hydrocarbons produced by the co-fractionation of step (f) is subjected to a single step of hydrotreatment without any associated depentanizing.

In another embodiment, a stream containing C4 hydrocarbons is optionally selectively hydrogenated and then the optionally selectively hydrogenated stream is fractionated to separate a 2-butene stream from a first 1-butene stream.

In another embodiment, the 2-butene stream is cracked with the first stream containing C4 and higher hydrocarbons.

In yet another embodiment, the isobutylene in the 1-butene stream is reacted with methanol to produce MTBE and the MTBE is recovered separately from a second 1-butane stream.

In still another embodiment, the second 1-butene stream is fractionated to produce a 1-butene product stream separate from a C4 paraffins stream.

In another embodiment, the present invention provides a process for recovering 1-butene from a C4 hydrocarbon stream recovered by separation from reaction products of an oxygenate-to-olefin synthesis, the C4 hydrocarbon stream containing butane, isobutylene, 1-butene and 2-butene, wherein the process comprises:

(a) optionally selectively hydrogenating the C4 hydrocarbon stream;
(b) fractionating the optionally selectively hydrogenated C4 hydrocarbon stream to separate a 2-butene stream from a first 1-butene stream;
(c) reacting isobutylene in the first 1-butene stream with methanol to produce MTBE;
(d) separating MTBE from a second 1-butene, and
(e) fractionating the second 1-butene stream to produce a 1-butene product stream separate from a butane stream.

These and other embodiments will be apparent from the present specification as set forth in the following description. Still other embodiments will be apparent to those of ordinary skill in the art after consideration of the specification.

Figure 1:
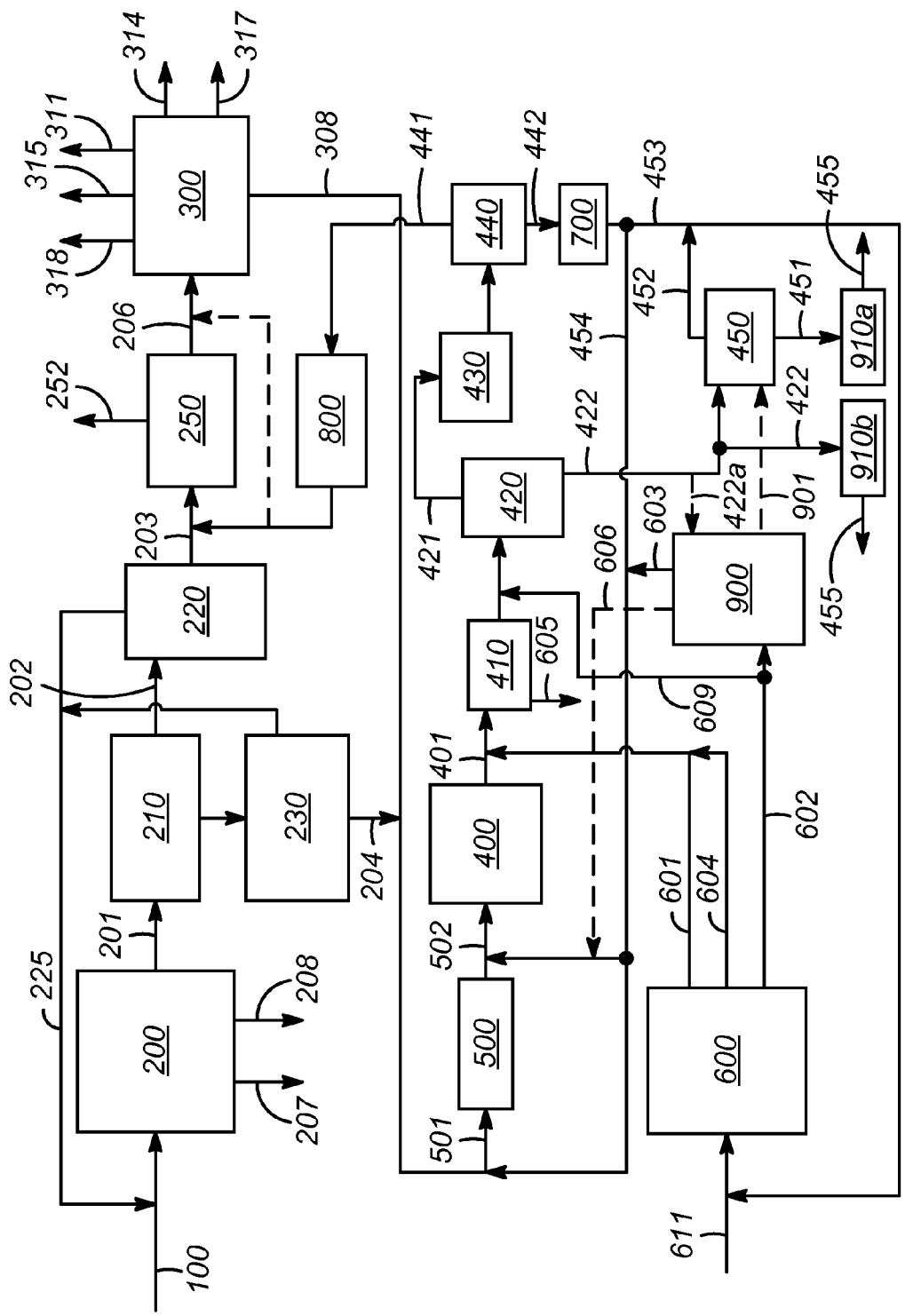
FIG. 1 illustrates simplified schematic process flow diagram of an integrated MTO and hydrocarbon pyrolysis process for making light olefins.

Those skilled in the art, guided by the teachings provided by this specification, will recognize and appreciate that the illustrated systems or process flow diagrams have been simplified by the elimination of various usual or customary pieces of process equipment including heat exchangers, process control systems, knock-out drums, pumps, certain fractionation system details such as column designs, column reboilers, overhead condensers, and the like. It also will be appreciated that the simplified process flow diagrams depicted in the figures may be modified in many aspects, such as by using features in one figure as an alternative in another figure, without departing from the basic overall concept of the invention, which is limited only by the claims.

DETAILED DESCRIPTION OF THE INVENTION

The present invention provides an integrated MTO synthesis and hydrocarbon pyrolysis system. The integration of a MTO system, including its complementary olefin cracking reactor, with a hydrocarbon pyrolysis reactor facilitates the flexible production of olefins and other petrochemical products, such as butene-1 and MTBE. These reactors are integrated with effluent separation and conditioning, olefin purification and recovery, hydrocarbon recycle to the various reaction zones, and C4 hydrocarbon processing methods, such as methyl tertiary butyl ether synthesis, and possibly isomerization, to provide a wide variety of olefins and olefins products as explained in more detail below.

The olefin cracking subsystem (OCR) of the overall MTO system has surprisingly facilitated the integration of the MTO system with the hydrocarbon pyrolysis system. While many difficulties would be expected to complicate the direct processing of a hydrocarbon pyrolysis effluent with the effluent of an oxygenate to olefins (MTO) reactor, it has been found that by using the OCR to conjointly treat the heavier fractions of the effluent of the oxygenate to olefins (MTO) reactor along with the lighter fractions of the effluent of the hydrocarbon pyrolysis system, one is able to successfully integrate the MTO system with the hydrocarbon pyrolysis system and maximize the production of light olefins.

One particular benefit flowing from the integration of a MTO system with the hydrocarbon pyrolysis system is that the integration facilitates the ability to expand the operation of the hydrocarbon pyrolysis system without having to expand the hydrocarbon pyrolysis system compressor section, i.e., the integration decouples the compression. This result is accomplished by taking advantage of the OCR compressor section for processing at least a portion of the light olefin-containing cracked gas effluent of the hydrocarbon pyrolysis system, or eliminating the compression section of the hydrocarbon pyrolysis system altogether.

Normally, the OCR section has a smaller capacity than the MTO system. By integrating the MTO system and the hydrocarbon pyrolysis system, the OCR section becomes of comparable capacity and significant economies of scale are realized.

As illustrated in FIGS. 1 through 4, cracker products recovered from the hydrocarbon pyrolysis reactor effluent, and particularly products produced by a naphtha steam cracker, are converted to valuable ethylene and propylene in an olefin cracking reactor and its related separation sub-system and ultimately are sent to the MTO fractionation system for recovery.

With reference to FIG. 1, one embodiment of an integrated MTO-hydrocarbon pyrolysis system will be described.

As shown in FIG. 1, an oxygenate feed (100), usually methanol, is fed to the oxygenate conversion (MTO) reactor (200). While the feedstock to the oxygenate conversion reactor could contain one or more aliphatic-containing compounds that include alcohols, amines, carbonyl compounds for example aldehydes, ketones and carboxylic acids, ethers, halides, mercaptans, sulfides, and mixtures thereof; it generally will be composed of a purified stream of light oxygenates such as one or more of methanol, ethanol, dimethyl ether, diethyl ether, or combinations thereof. By far, the most widely used oxygenate feed material is methanol.

In the oxygenate conversion (MTO) reactor (200), the oxygenate feed, e.g., methanol is contacted with a molecular sieve catalyst, usually a silicoaluminophosphate (SAPO) molecular sieve catalyst, under conditions designed to convert the oxygenate feed into predominately light olefins. As used herein, references to "light olefins" are to be understood to generally refer to C2 and C3 olefins, i.e., ethylene and propylene, alone or in combination. In particular, the oxygenate conversion reactor section produces or results in formation of an oxygenate conversion reactor effluent stream which generally comprises fuel gas hydrocarbons such as methane, ethane and propane, light olefins, and C4+ hydrocarbons.

A non-limiting list of suitable SAPO molecular sieve catalysts includes SAPO-17, SAPO-18, SAPO-34, SAPO-35, SAPO-44, and mixtures thereof. The equipment and conditions with which this conversion reaction is conducted are well known to those skilled in the art and do not need to be detailed here. Numerous patents describe this process for various types of these catalysts including U.S. Pat. No. 3,928,483; U.S. Pat. No. 4,025,575; U.S. Pat. No. 4,252,479; U.S. Pat. No. 4,496,786; U.S. Pat. No. 4,547,616; U.S. Pat. No. 4,677,242; U.S. Pat. No. 4,843,183; U.S. Pat. No. 4,499,314; U.S. Pat. No. 4,447,669; U.S. Pat. No. 5,095,163; U.S. Pat. No. 5,191,141; U.S. Pat. No. 5,126,308; U.S. Pat. No. 4,973,792; and U.S. Pat. No. 4,861,938, the disclosures of which are incorporated herein by reference.

In general, the process for converting an oxygenate feedstock in the presence of a molecular sieve catalyst can be carried out in a variety of reactors, including as representative examples a fixed bed process, a fluidized bed process (includes a turbulent bed process), a continuous fluidized bed process, and a continuous high velocity fluidized bed process.

As noted, in addition to light olefins, the effluent stream from the oxygenate conversion reaction also typically includes methane, ethane, propane, DME, C4 olefins and saturates, C5+ hydrocarbons, water and other hydrocarbon components in minor amounts.

The effluent stream containing the light olefin products is usually directed to a quench unit (not shown) wherein the effluent stream is cooled and water and other condensable components are condensed. The condensed components, which comprise a substantial amount of water, typically are circulated through a recirculation line (not shown) back to the top of the quench unit. The condensed components includes water to treatment 207 and stripped water 208.

The light olefin-containing effluent stream (201), ultimately recovered from the overhead of the quench unit then is compressed in one or more stages (e.g., in one or more compressors) in a compression zone (210) to form a compressed effluent stream (202). Typically, after each stage of compression, the compressed stream is cooled causing the condensation of heavier components which can be collected in one or more knock out drums between compression stages. In connection with oxygenate treatment or recovery zones (220 and 230), the respective vapor and liquid fractions can be processed using one or more sections or unit operations such as are well-known to those skilled in the art to isolate, separate, remove and/or recycle various materials, such as, for example, excess and by-product oxygenate materials and water. The light olefins are recovered as a first light olefin stream (203) separate from oxygenates (225), which can be recycled to the oxygenate conversion reactor, and from other heavier components (204) (i.e., a first stream containing C4 and higher hydrocarbons (C4+ hydrocarbons) and which typically includes a quantity of butenes, such as 1-butenes, 2-butenes and isobutenes), at least a portion of which are routed to an olefin cracking reactor (400) as described in more detail below.

The first light olefin stream (203) then is conditioned to remove acid gases ($CO_2$ and $H_2S$) and the stream is dried before it is fractionated. Acid gas removal is commonly accomplished using a caustic scrubber (250), the operation of which is so well known to those skilled in the art that further description is unwarranted.

Figure 2:
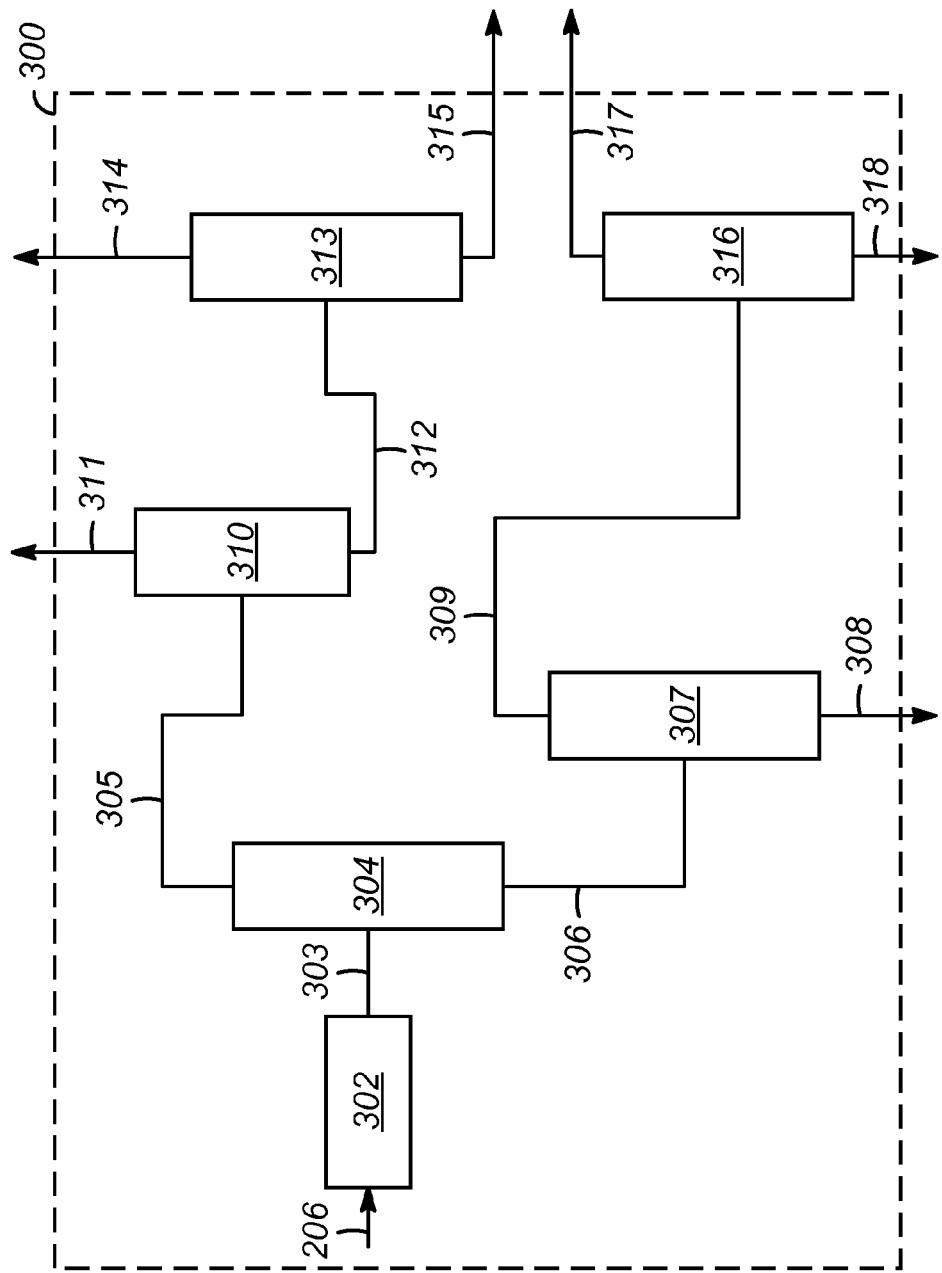
FIG. 2 shows a simplified schematic process flow diagram of one embodiment of a C2/C3 separation system for the integrated MTO and hydrocarbon pyrolysis process of the present invention.

The conditioned product stream (conditioned stream) (206) is directed to a C2/C3 separation system (300)—See FIG. 2 for additional details, for separating the conditioned stream (206) into ethylene and propylene products, (314) and (317) respectively. As shown in FIG. 2, the C2/C3 separation system includes a drier unit (302) for completing the drying of the conditioned stream (206) and typically includes one or more cryogenic fractionation columns. Olefin purification from hydrocarbon containing streams is well known to those skilled in the art. Typically, the gaseous effluent is compressed and then chilled and passed through a series of pressurized fractionators to separate the effluent into streams rich in its component parts, e.g., hydrogen, methane, ethane, propane, ethylene, propylene, and mixed C4 hydrocarbon streams, as is known to those of ordinary skill in the art. Alternatively, other separation processes known to those skilled in the art, including, but not limited to, extractive distillation, selective membrane separation and/or molecular sieve separation also can be advantageously used. The present invention is not limited to any particular separation procedure or arrangement.

Although the order of fractionation can vary, FIG. 2 presents one suitable embodiment for fractionating the conditioned and dried product stream (303). In particular, the conditioned and dried product stream (303), or a select portion thereof, can be passed to a deethanizer column (304). In the deethanizer column, the conditioned and dried product stream is fractionated, such as by conventional distillation, to provide a deethanizer overhead stream (305) comprising C2 and lighter hydrocarbons (i.e., C2− hydrocarbons, including methane, acetylene, ethane, ethylene, and possibly also some inert species ($N_2$, CO, etc.), and a deethanized C3+ bottoms stream (306) comprising components enriched in compounds heavier than ethane, such as propylene, propane, mixed butenes and/or butane.

The deethanizer overheads stream (305) can be treated to remove acetylene (not shown) and ultimately is passed to a demethanizer column (310). In the demethanizer column, the C2− hydrocarbon product is fractionated, such as by conventional distillation, to provide a demethanizer overhead stream (311) predominantly comprising C1− hydrocarbons including methane, but also including some ethane, and ethylene (which can be separately recovered from the stream, for example, by known adsorption processes—not shown), and a demethanized C2+ bottoms stream (312) comprising predominately ethylene and ethane.

The demethanized C2+ bottoms stream (312), or at least a portion thereof, is passed to a C2-splitter. In the C2-splitter, the demethanizer bottoms stream is treated, e.g., is fractionated, such as by conventional distillation, to provide an overhead ethylene product stream (314) and a bottoms stream (315), principally composed of ethane. The ethane-containing bottoms stream, or a portion thereof can advantageously be recycled to the hydrocarbon pyrolysis reactor, or can alternatively be used as fuel.

The deethanized C3+ bottoms stream (306) or at least a portion thereof, is passed to a depropanizer column (307). In the depropanizer column, the deethanized C3+ bottoms stream can be treated or fractionated, such as by conventional distillation, to produce a depropanizer overhead stream (309) comprising C3 materials and a depropanized stream (308) generally comprising C4+ components (a stream containing C4 hydrocarbons). As described below, at least a portion of this C4+ stream (i.e., stream containing C4 hydrocarbons) can be processed through an olefin cracking reactor (400) in order to increase the production of light olefins, particularly propylene.

The depropanizer overhead stream (309), or at least a portion thereof, is passed to a C3− splitter (316). In some embodiments, the depropanizer overhead stream (309) may next undergo oxygenate removal (not shown) to remove any dimethyl ether (DME) and other trace oxygenates from the C3-containing overhead before it is separated in the C3− splitter (316). In the C3− splitter, the depropanizer overhead stream is treated, e.g., is fractionated, such as by conventional distillation, to provide an overhead propylene product stream (317) and a bottoms stream (318), generally composed of propane. The propane-containing bottoms stream, or a portion thereof can advantageously be recycled to the hydrocarbon pyrolysis reactor, or alternatively can be used as fuel.

Thus, the C2/C3 separation system usually produces a fuel gas stream (311), an ethane stream (315), a propane stream (318), an ethylene product stream (314), a propylene product stream (317) and a stream containing C4 hydrocarbons (308). The fuel gas stream generally includes the majority of the methane and hydrogen that was present in the dry product stream. The ethylene and/or propylene are suitable as feedstocks for the formation of polyethylene and/or polypropylene and/or other copolymers. The fuel gas stream optionally is burned as a fuel in one or more of the steps of the integrated process.

In order to maximize the production of light olefins from the stream containing C4 hydrocarbons (308) in the illustrated embodiment, this stream is first subjected to a step of selective hydrogenation in the selective hydrogenation reactor (500) in order to catalytically convert diolefins (e.g., butadiene) and acetylenes in the stream containing C4 hydrocarbons to butenes. The stream containing C4 hydrocarbons is passed to the selective hydrogenation reactor to convert diolefins, and especially butadienes, to olefins, and to create a diolefin reduced stream (502) which is passed to an olefin cracking reactor (400). Conditions and catalysts to employ in the selective hydrogenation reactor (500) will be recognized by those skilled in the art.

The olefin cracking reactor (OCR) (400) constitutes an integral piece of the MTO process and provides a way for increasing the overall yield of light olefin from the oxygenate feed (and the pyrolysis feed described below). The design and conditions of operation of an olefin cracking reactor, including the selection of a suitable catalyst, are well understood by those skilled in the art. U.S. Pat. No. 6,646,176, the description of which is incorporated herein by reference, exemplifies suitable catalysts and operating conditions. Other catalysts and operating parameters will be recognized by those skilled in the art and the present invention is not limited to any particular method. The olefin cracking reactor (400) converts larger olefins, including C4 olefins and larger hydrocarbons, including higher olefins and paraffins, to light olefins, primarily propylene. The production of light olefins from the olefin cracking reactor does not consume ethylene. When the feed to the OCR contains a significant amount of C5+ olefins, the olefin cracker reactor also produces additional butenes.

In accordance with the present invention, the described MTO process is integrated with a hydrocarbon pyrolysis (cracking) reaction system. Processes for non-catalytically cracking and catalytically cracking hydrocarbon feedstocks are well known.

Steam cracking in a furnace and cracking in contact with hot non-catalytic particulate solids are two well-known non-catalytic thermal cracking processes. Fluid catalytic cracking and deep catalytic cracking are two well-known catalytic cracking processes.

Thus, as used herein, hydrocarbon pyrolysis is used in a broader sense to embrace a variety of thermal cracking techniques, including both steam cracking, as well as catalytic cracking (such as fluid catalytic cracking (FCC)) procedures.

As used herein, hydrocarbon pyrolysis thus involves sufficiently heating the feedstock usually in the presence of steam, or in the presence of a catalyst, to cause thermal decomposition of the larger hydrocarbon molecules. Steam cracking processes are generally carried out in radiant furnace reactors at elevated temperatures for short residence times while maintaining a low reactant partial pressure, relatively high mass velocity, and effecting a low pressure drop through the reaction zone. Again, cracking processes are well known to those skilled in the art and additional details are not necessary for a full understanding of the present invention. The present invention is particularly useful for integrating a steam pyrolysis reactor operating with a naphtha feedstock (611) with an MTO system.

Common feedstocks for a hydrocarbon pyrolysis system include gaseous or liquid hydrocarbon materials like naphtha, liquefied petroleum gas (LPG), propane, ethane, raffinate, gas condensates, atmospheric gas oils and hydrocracker bottoms.

While the products produced in the pyrolysis reactor depend on the composition of the feed, the cracking temperature, the reactor (furnace) residence time and in the case of steam cracking, the hydrocarbon to steam ratio, as recognized by those of ordinary skill in the art, the effluent from the pyrolysis reactor will include a cracked gas that typically contains light olefins (a second cracked gas effluent stream containing light olefins), and C4's, and the pyrolysis reactor effluent also often contains higher paraffins and aromatic hydrocarbons as well.

Following conventional quenching operations and initial fractionation, commonly including both an oil quench and a water quench, the pyrolysis effluent typically is separated into a cracked gas effluent stream containing light olefins (601), i.e., the second cracked gas effluent stream; often a pyrolysis gasoline fraction (602) (pygas stream); and water and fuel oil by-products. In the prior art, the cracked gas effluent is generally compressed, conditioned, e.g., treated to remove acid gas ($CO_2$ and $H_2S$) and dried, and then is subjected to a variety of fractionations to produce ethylene and propylene products, as well as other products such as butadiene. The pyrolysis gasoline or pygas also is treated, by for example a hydrotreating process, to upgrade its value for use in producing gasoline, or for generating additional light olefins.

In accordance with the present invention, the processing of the cracked gas effluent stream (second cracked gas effluent stream containing light olefins) (601) and the pygas stream (602), when available from the pyrolysis reactor are integrated into and processed within the MTO system. This integration permits the sharing of compressors and fractionation equipment associated with the MTO system. Integration of the MTO and the hydrocarbon pyrolysis system also facilitates maximum ethylene and/or propylene production through the routing of various feed streams and the judicious arrangement of recycle streams to appropriate cracking zone(s), e.g. ethane/propane to the pyrolysis reactor and C4+ olefins to the olefin cracking reactor (400). For example, with the availability of the olefin cracking reactor (400) of the MTO system, additional propylene can be produced from a pyrolysis gas (pygas) stream that is often available from the hydrocarbon pyrolysis reactor and especially from a naphtha steam cracker.

One surprising aspect discovered in connection with the present invention is that most of the sulfur contaminants that are introduced with the effluent streams obtained from the hydrocarbon pyrolysis system, i.e., the second cracked gas effluent stream and the pyrolysis gasoline stream, tend to be concentrated in the heavier hydrocarbon fractions, especially fractions containing the bulk of the C6 and heavier hydrocarbons, and are passed through the various fractionation stages and ultimately discharged without creating serious problems in the various catalytic operations. Any residual sulfur contaminants seem to be easily removed either by a regenerative pre-scrubber designed to remove acid gases ($CO_2$ and $H_2S$), such as in a monoethanolamine (MEA) absorber/stripper, or by the conventional caustic scrubber in the MTO system.

In particular, in the embodiment shown in FIG. 1, the cracked gas effluent stream containing light olefins (601) generated from the pyrolysis reactor is added to the effluent (401) from the olefin cracking reactor (first cracked gas effluent stream containing light olefins). In this way, the combined stream is then processed in the olefin cracking compression zone (410) for preparing the stream for product fractionation in the recycle column (420). The olefin cracking compression zone (410) may be one or more compression stages. In the recycle column (420), the compressed combination of the OCR effluent and the pyrolysis reactor cracked gas effluent is treated, e.g., is fractionated, such as by conventional distillation, to provide an overhead C5– stream (first stream containing C5 and lighter hydrocarbons) (421) and a bottoms C5+ stream (first stream containing C5 and higher (heavier) hydrocarbons) (422).

The bottoms stream (422) is treated, e.g., is fractionated, such as by conventional distillation, in a depentanizer column (450) to provide an overhead stream (452) (i.e., a second stream containing C4 hydrocarbons) that can be recycled to the pyrolysis reactor and a bottoms of C6+ (C6 and higher (heavier) hydrocarbons) (451) that has value as gasoline, or alternatively may be further processed to recover aromatic compounds.

The overhead C5– stream (421) (first stream containing C5 and lighter hydrocarbons) produced in the recycle column (420) is subjected to a second stage of compression in compression zone (430), comprising one or more compression stages and then is passed to a depropanizer column (440). In the depropanizer column, the compressed C5– overheads stream can be treated or fractionated, such as by conventional distillation, to produce a depropanizer overhead stream (441) comprising C3– hydrocarbons enriched in light olefins (a second light olefins stream) and a depropanized stream (442) generally comprising C4 and C5 hydrocarbon components (a second stream containing C4 and higher hydrocarbons). The depropenized stream (442) is then selectively hydrogenated in the selective hydrogenation reactor (700) in order to catalytically convert diolefins (e.g., butadiene) and acetylenes in the depropanized stream (442) to butenes.

One part of the hydrogenated effluent (453) can be recycled as additional feedstock to the pyrolysis reactor (600), while, depending on the extent of hydrogenation, another part (454) can be recycled for blending with the first stream containing C4 and higher hydrocarbons (204) and with the depropanized stream (308) generally comprising C4+ components (stream containing C4 hydrocarbons), which together form the feed stream for the selective hydrogenation reactor (500). Depending upon the extent of hydrogenation in reactor (700), it may be possible to send the stream (454) directly to the OCR (400), by-passing reactor (500).

The combined C4 and higher hydrocarbon stream (501) is passed to the selective hydrogenation reactor (500) to convert diolefins, and especially butadienes, to olefins, and to create a diolefin reduced stream (502) which is passed to the olefin cracking reactor (400). As noted above, conditions and catalysts to employ in the selective hydrogenation reactor will be recognized by those skilled in the art.

The depropanizer overhead stream (441) comprising C3– hydrocarbons and enriched in light olefins (second light olefin stream) is optionally treated in a regenerative pre-scrubber (800) to remove acid gases ($CO_2$ and $H_2S$), such as in a monoethanolamine (MEA) absorber/stripper (800), before blending with the first light olefin stream (203) for additional treatment in the caustic scrubber (250). Depending upon the quantity of acid gas, and especially $H_2S$ in the depropanizer overhead stream (441), in some cases it might be possible to dispense with the regenerative pre-scrubber (800) and blend the depropanizer overhead stream (441) directly with the first light olefin stream (203) for treatment directly in the caustic scrubber (250). Alternatively, in some cases the treatment in pre-scrubber (800) may be sufficient to allow the treated second light olefin stream to bypass the caustic scrubber (250) and be blended directly with the conditioned stream (206) feeding the C2/C3 separation system.

In circumstances where there also is a pygas effluent stream (602) recovered separately from the effluent of the pyrolysis reactor (600), the present invention also provides ways of integrating the processing (upgrading) of the pygas stream with the MTO system. As shown in the embodiment of FIG. 1, the pygas effluent stream (602) can first be treated in a pygas hydrotreater (900) and depending on the sufficiency of the treatment the hydrotreater effluent can either be passed in stream (603—solid line) to the selective hydrogenation reactor (500) and then to the olefin cracking reactor (400), or in stream (606—dashed line) directly to the olefin cracking reactor (400).

In the olefin cracking reactor (OCR), C4 olefins and larger hydrocarbons, including higher olefins and paraffins, in the pygas (as well as in the other C4-containing streams delivered the OCR) are converted to light olefins, primarily propylene. Since the pygas tends to contain a significant amount of C5+ olefins, the olefin cracker reactor also produces additional butenes.

An alternate embodiment, also shown in FIG. 1, for processing a pygas effluent stream (602) is when it is separately available from the effluent of the pyrolysis reactor (600). Other than the manner of handling the pygas stream and the recycle columns bottoms (422), the embodiment is substantially similar in other respects to the first embodiment of FIG. 1. As a result, only a few of the streams and unit operations differ.

As shown in this embodiment, when the pygas effluent stream (609) is available as a liquid feed, it can be pumped to high pressure, vaporized and delivered directly to pressurized effluent from the olefin cracking reactor (400). This processing reduces the load on the olefin cracking compressors. This processing also benefits both the pygas hydrotreater (900) and the selective hydrogenation reactor (500), as the previous removal of C6+ hydrocarbons from the stream before hydrotreating optimizes the consumption of hydrogen in the hydrotreater and allows the hydrotreated stream (452) to by-pass the selective hydrogenation reactor (500). In addition, to the extent there are heavy contaminants in the pygas stream, this processing facilitates their removal in the bottoms (422) from the recycle column (420) and ultimately in the C6+ product in stream (451).

Figure 3:
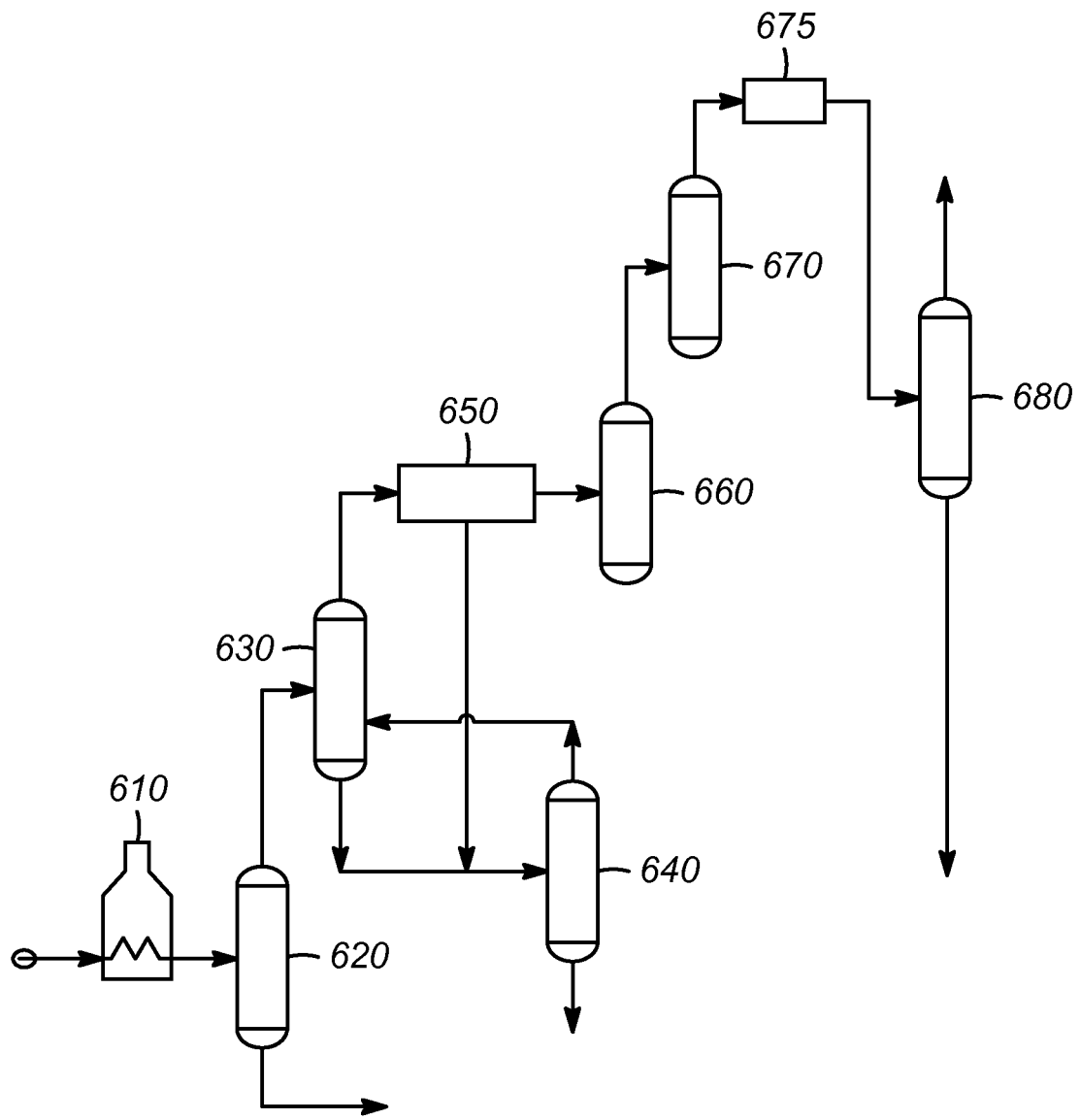
FIG. 3 illustrates a simplified schematic process flow diagram of a typical (conventional) hydrocarbon pyrolysis reactor (cracker) flow scheme.

An alternative, or third, embodiment useful when the hydrocarbon pyrolysis reactor does not produce a separate pygas effluent stream. In this case, the principal stream from the pyrolysis reactor section (600) entering the MTO-OCR section is the overhead stream from the water quench of the pyrolysis reactor (604). FIG. 3 illustrates a simplified schematic process flow diagram of a typical (conventional) hydrocarbon pyrolysis reactor (cracker) flow scheme. A typical pyrolysis reactor system (600) passes a hydrocarbon feed to a pyrolysis furnace (610) generating a pyrolysis effluent stream. The effluent stream is passed to a fractionation unit (620) generating an overhead process stream and a fuel/oil bottoms stream. The overhead process stream is passed to a water quench unit (630) where the stream is cooled and liquid is knocked out. The quench bottoms are passed to a stabilizer (640) where quench water is recovered and recycled. The quench overhead is compressed in a series of compression stages (650). The compressed stream is passed through an amine treater (660), a caustic scrubber (670), a dryer (675), and then passed to a depropanizer (680) to generate a C3– overhead stream and a C4+ bottoms stream. In the context of this embodiment, at least a portion of the overhead from the water quench unit operation is delivered directly to the MTO-OCR section of the integrated process, rather than undergoing typical compression in the cracker compressor zone. This overhead stream will typical comprise C8– hydrocarbons, i.e., C8 and lighter hydrocarbons.

As shown in this embodiment, the overhead of the water quench from the pyrolysis reactor section (600) is passed to the first stage of the compressor section (410) following the OCR (400). As a consequence of this compression, heavier hydrocarbons, predominantly C6+, are condensed, recovered in the first stage knock-out drum, and returned via stream (605) to the pyrolysis section for further processing. A significant fraction of sulfur contaminants that originate in the overhead of the water quench from the pyrolysis reactor should be eliminated with this stream. The C5– portion of the pyrolysis reactor water quench overhead then is co-processed with the remainder of the OCR effluent.

This combined stream is then processed for product separation in the recycle column (420). In the recycle column, the compressed combination of the OCR effluent and the residual pyrolysis reactor water quench effluent is treated, e.g., is fractionated, such as by conventional distillation, to provide an overhead C5– stream (421) and a bottoms pygas, C5+ stream (422). Since a sizeable level of sulfur contaminants may yet reside in the recycle column feed, this embodiment contemplates operating the recycle column so that most of those contaminants are discharged with the recycle column bottoms (pygas) in stream (422) for treatment in a first stage pygas hydrotreater as described below.

In accordance with this embodiment, the bottoms pygas stream (422a) first is treated in stage 1 of a pygas hydrotreater (900). The hydrotreatment of the bottoms C5+ stream (422) is typically conducted over a Group VIII metal catalyst (e.g., iron, cobalt, nickel, ruthenium, rhodium, palladium, osmium, iridium, and/or platinum) to hydrogenate components generally considered gum precursors such as diolefins, acetylenics, styrenics, dicyclopentadiene, and the like. As is known, the hydrogenation tends to be selective such that no significant amounts of mono-olefins, aromatics, and other gasoline octane enhancers are hydrogenated. Typically, paraffins are left unchanged or mildly isomerized which can help gasoline value. Sulfur contaminants also tend to be converted to $H_2S$.

In accordance with this embodiment, the effluent hydrotreated pygas stream (901) from the first stage of hydrotreating is then depentanized in depentanizer (450), ostensibly to make a clean separation between C5– hydrocarbons and the C6+ hydrocarbons. In particular, in the depentanizer (450) the effluent from the first stage of pygas hydrotreating is fractionated, such as by conventional distillation, to provide an overhead stream (452), containing C5+ hydrocarbons. This C5+ hydrocarbon stream can be processed in several ways (not shown). Depending on the diene level in stream (452) it can be pumped either to selective hydrogenation reactor (700) or (500), or bypass both and be pumped directly to the olefin cracking reactor (400). The bottoms from the depentanizer column in stream (451), predominantly comprising C6+ hydrocarbons is typically subjected to a second stage of hydrotreatment (910a) in order to saturate the olefins and de-sulfurize the pygas. The hydrotreated pygas is discharged in stream (455), where it is typically processed for aromatics extraction and/or motor gasoline pool addition.

In an alternative embodiment, the first stage of pygas hydrotreating and the depentanizer are eliminated altogether. This arrangement would provide a substantial capital cost reduction. This arrangement can be used when the added sulfur load introduced into the OCR section by the pyrolysis reactor water quench overhead is not too severe.

In this case, the recycle column (420) is operated so that the bulk of the sulfur contaminants are removed from the OCR section in the bottoms (422) of the recycle column (420). With sulfur no longer a concern, the selective hydrogenation reactors (700) and (500) should be sufficient for stabilizing the C4-C5 hydrocarbons recovered from depanizer (440), at least a portion of which is recycled to the OCR section (400).

In this embodiment, the bottoms (422) of the recycle column (420) predominantly comprising C6+ hydrocarbons is subjected to a second stage of hydrotreatment (910b). The hydrotreated pygas is discharged in stream (455), where it is typically processed for aromatics extraction and/or motor gasoline pool addition.

Figure 4:
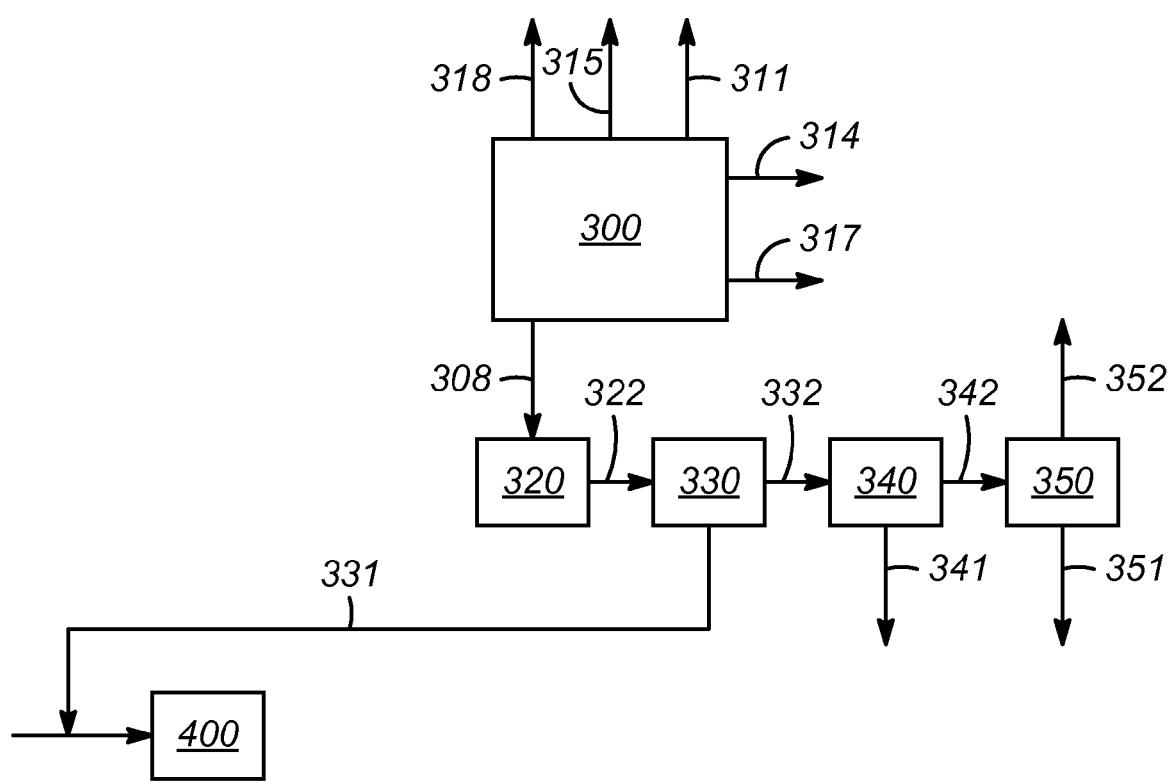
FIG. 4 illustrates another alternative simplified schematic process flow diagram of an integrated MTO and hydrocarbon pyrolysis process for making light olefins.

Turning now to FIG. 4, a processing option made possible because of the integration of the hydrocarbon pyrolysis system, and particularly a naphtha steam cracker, with the MTO-OCR is illustrated where additional MTO products that are not diluted with cracker effluent processing, i.e., MTO products that are segregated from the integration with the hydrocarbon pyrolysis system, are converted into desirable products including 1-butene and MTBE. FIG. 4 is presented as an alternative processing option to the third embodiment with most of the processing details which are not altered in the third embodiment system eliminated for clarity. As will be recognized by those skilled in the art, the FIG. 4 process also is amenable to integration with other systems, including FIG. 1 which provides a suitable similar C4 hydrocarbon stream for processing.

In addition to ethylene and propylene, both the MTO system and the integrated hydrocarbon pyrolysis reactor/olefin cracking reactor produce 1-butene and other C4 hydrocarbons. With additional processing, the C4 olefins from the MTO system in particular can be processed to yield MTBE and 1-butene as separate products.

There is an advantage of processing the C4 olefins produced from MTO system separate from those C4 olefins produced in the cracker effluent and in the olefin cracking reactor. MTO product contains a relatively low fraction of isobutene and saturated compounds in the C4 fraction compared to cracker effluent. Based on relative volatilities, a purified 1-butene product, free of isobutene, can not be obtained using conventional distillation. Separation of 1-butene from isobutene typically requires preferential reaction of the isobutene (e.g., to make MTBE) followed by distillation to recover unreacted 1-butene. Production of 1-butene preferentially from the MTO C4+ product is advantageous for 1-butene recovery as the capital and energy requirements for separation are minimized due to the fact that less isobutene and saturates are produced during the oxygenate-to-olefin reaction and thus there are less of these components to be removed from the 1-butene product. Alternatively, if additional 1-butene production is desired, 1-butene may be recovered from the combination of MTO effluent C4+, the C4 products from the hydrocarbon cracker (hydrocarbon pyrolysis system) and from the olefin cracking reactor (OCR) at additional cost for processing larger streams.

The C4+ hydrocarbon stream (308) recovered from the depropanizer column (307) of the C2/C3 separation system (300) typically contains at least 15% by weight 1-butene, usually at least 20% by weight 1-butene and often, at least 22 weight percent 1-butene. In addition, this stream typically contains less than 10% by weight isobutylene, usually less than 9% by weight isobutylene and often less than 8% by weight isobutylene. Both butadiene and butanes are also very low, typically each is less 5% by weight and usually less than 3% by weight of stream (308). As shown in FIG. 4, rather that recycling all of the C4+ hydrocarbons recovered from the depropanizer column (307) of the C2/C3 separation system (300) to the olefin cracking reactor, stream (308) is first subjected to a step of selective hydrogenation in the selective hydrogenation reactor (320) in order to catalytically convert diolefins to olefins, primarily butadiene to butenes, in the C4 and higher hydrocarbon stream (308). In order to minimize olefin loss, it will often be advantageous to use a palladium-based catalyst in reactor (320), such as a palladium on alumina catalyst.

With reference to FIG. 4, the effluent from reactor (320) is passed in stream (322) to a B-2 column (330) where the 2-butene and heavier hydrocarbons are separated, e.g., are fractionated, such as by conventional distillation, from isobutylene and 1-butene. The 2-butene enriched stream (331) is recycled to the olefin cracking reactor (400); while stream (332) containing isobutylene and 1-butene is passed to an MTBE synthesis reactor (340).

In accordance with this invention, the isobutylene in stream (332) then is reacted with methanol to make MTBE. Converting the isobutylene in stream (332) to methyl tertiary butyl ether by reaction with methanol can be carried out in a number of ways well known to those skilled in the art and any particular synthesis process may be employed in the practice of the present invention. The MTBE synthesis reaction can be performed in fixed-beds, or more preferably in an arrangement employing a reactive-distillation column, using a strong acid catalyst (such as UOP's EtherMax™ process for MTBE synthesis). The process usually employs an acid type ion exchange resin, such as a high molecular weight carbonaceous material containing sulfonate groups —$SO_3H$. Suitable sulfonated resins of various types are available from a variety of commercial sources under various commercial names, such as Amberlyst-15 available from Rohm & Hass, a wholly owned subsidiary of The Dow Chemical Company.

The MTBE product is recovered in stream (341) separately from the more volatile materials including 1-butene in stream (342). As an alternative, a portion of the MTBE product could thereafter be back-cracked to isobutylene. Stream (342), from which the isobutylene has now been depleted, is passed to a B-1 column (350), where a 1-butene product (351) is separated, e.g., by fractionation, such as by using conventional distillation, from the more volatile C4 paraffins in stream (352), which can be recycled to the hydrocarbon pyrolysis (cracker) reactor.

It will be understood that while the invention has been described in conjunction with specific embodiments thereof, the foregoing description is intended to illustrate, but not limit the scope of the invention.

In further embodiments, the present invention comprises:
1. A light olefins synthesis process comprising:
   (a) passing an oxygenate feed to an oxygenate-to-olefin reactor to contact the oxygenate feed with a molecular sieve catalyst and to convert oxygenate feed to light olefins which are discharged from the oxygenate-to-olefin reactor in an effluent stream;
   (b) separating the effluent stream into a first light olefins stream separate from a first stream containing C4 and higher hydrocarbons;

(c) selectively hydrogenating and then cracking the first stream containing C4 and higher hydrocarbons to form a first cracked gas effluent stream containing light olefins;
(d) separately cracking a hydrocarbon stream to form a second cracked gas effluent stream containing light olefins;
(e) co-fractionating the first and second cracked gas effluent streams to produce a second light olefins-containing stream separate from a second stream containing C4 and higher hydrocarbons;
(f) co-conditioning the first and second light olefins-containing streams to remove acid gases and produce a conditioned stream; and
(g) separating the conditioned stream into an ethylene product stream, a propylene product stream and a stream containing C4 hydrocarbons.

2. The light olefins synthesis process of each of the previous embodiments and subsequent embodiments 3-14 (individually and in combination) wherein the separate cracking of step (d) comprises a stream pyrolysis of a feed comprising one or more of naphtha, liquefied petroleum gas (LPG), propane, ethane, raffinate, gas condensates, atmospheric gas oils and hydrocracker bottoms.

3. The light olefins synthesis process of each of the previous embodiments and subsequent embodiments 4-14 (individually and in combination) wherein at least a portion of the second stream containing C4 and higher hydrocarbons is cracked with the first stream containing C4 and higher hydrocarbons.

4. The light olefins synthesis process of each of the previous embodiments and subsequent embodiments 5-14 (individually and in combination) wherein at least a portion of the second stream containing C4 and higher hydrocarbons is selectively hydrogenated and then cracked with the first stream containing C4 and higher hydrocarbons.

5. The light olefins synthesis process of each of the previous embodiments and subsequent embodiments 6-14 (individually and in combination) wherein at least a portion of the stream containing C4 hydrocarbons separated in step (g) is recycled to be cracked with the first stream containing C4 and higher hydrocarbons.

6. The light olefins synthesis process of each of the previous embodiments and subsequent embodiments 7-14 (individually and in combination) wherein at least a portion of the second stream containing C4 and higher hydrocarbons is cracked with the hydrocarbon stream.

7. The light olefins synthesis process of each of the previous embodiments and subsequent embodiments 8-14 (individually and in combination) wherein the separate cracking of the hydrocarbon stream of step (d) forms both the second cracked gas effluent stream containing light olefins and a pyrolysis gas stream containing C4 and higher hydrocarbons.

8. The light olefins synthesis process of each of the previous embodiments and subsequent embodiments 9-14 (individually and in combination) wherein the pyrolysis gas stream containing C4 and higher hydrocarbons is selectively hydrogenated to produce a third stream containing C4 and higher hydrocarbons, and the third stream containing C4 and higher hydrocarbons is cracked with the first stream containing C4 and higher hydrocarbons.

9. The light olefins synthesis process of each of the previous embodiments and subsequent embodiments 10-14 (individually and in combination) wherein the pyrolysis gas stream containing C4 and higher hydrocarbons is blended with the first and second cracked gas effluent streams containing light olefins to produce a blended stream prior to the co-fractionation of step (e).

10. The light olefins synthesis process of each of the previous embodiments and subsequent embodiments 11-14 (individually and in combination) wherein the co-fractionation of step (e) comprises separating the first and second cracked gas effluent streams containing light olefins into a first stream containing C5 and lighter hydrocarbons and a first stream containing C5 and higher hydrocarbons.

11. The light olefins synthesis process of each of each of the previous embodiments and subsequent embodiments 12-14 (individually and in combination) wherein the first stream containing C5 and lighter hydrocarbons is treated to separate the second light olefins-containing stream from the second stream containing C4 and higher hydrocarbons.

12. The light olefins synthesis process of each of the previous embodiments and subsequent embodiments 13-14 (individually and in combination) wherein the co-fractionation of the blended stream of the pyrolysis gas stream containing C4 and higher hydrocarbons and the first and second cracked gas effluent streams containing light olefins prior produces the first stream containing C5 and lighter hydrocarbons and the first stream containing C5 and higher hydrocarbons.

13. The light olefins synthesis process of each of the previous embodiments and subsequent embodiment 14 (individually and in combination) wherein the first stream containing C5 and higher hydrocarbons is treated to separate a stream containing C6 and higher hydrocarbons from a stream containing C4 hydrocarbons 14. The light olefins synthesis process of each of the previous embodiments (individually and in combination) wherein the stream containing the C4 hydrocarbons is selectively hydrogenated and cracked with the first stream containing C4 and higher hydrocarbons.

In still further embodiments, the present invention comprises:

15. A light olefins synthesis process comprising:
(a) passing an oxygenate feed to an oxygenate-to-olefin reactor to contact the oxygenate feed with a molecular sieve catalyst and to convert oxygenate feed to light olefins which are discharged from the oxygenate-to-olefin reactor in an effluent stream;
(b) separating the effluent stream into a first light olefins stream separate from a first stream containing C4 and higher hydrocarbons;
(c) selectively hydrogenating and then cracking the first stream containing C4 and higher hydrocarbons to form a first cracked gas effluent stream containing light olefins;
(d) separately cracking a hydrocarbon stream to form a second cracked gas effluent stream containing light olefins, wherein the second cracked gas effluent stream containing light olefins comprises a stream containing C8 and lighter hydrocarbons produced as an overhead of a water quench;
(e) removing C6 and heavier hydrocarbons from the stream of C8 and lighter hydrocarbons by compression;
(f) co-fractionating the first cracked gas effluent stream and the second cracked gas effluent stream from which C6 and heavier hydrocarbons have been removed to produce a second light olefins-containing stream separate from a second stream containing C4 and higher hydrocarbons;

(g) co-conditioning the first and second light olefins-containing streams to remove acid gases and produce a conditioned stream; and (h) separating the conditioned stream into an ethylene product stream, a propylene product stream and a stream containing C4 hydrocarbons.

16. The light olefins synthesis process of embodiment 15 and each of the subsequent embodiments (individually and in combination) wherein the separate cracking of step (d) comprises a stream pyrolysis of a feed comprising a combination of one or more of naphtha, liquefied petroleum gas (LPG), propane, ethane, raffinate, gas condensates, atmospheric gas oils and hydrocracker bottoms.

17. The light olefins synthesis process of embodiments 15 and 16 and each of the subsequent embodiments (individually and in combination) wherein at least a portion of the second stream containing C4 and higher hydrocarbons is cracked with the first stream containing C4 and higher hydrocarbons.

18. The light olefins synthesis process of embodiments 15 through 17 and each of the subsequent embodiments (individually and in combination) wherein at least a portion of the second stream containing C4 and higher hydrocarbons is selectively hydrogenated and then cracked with the first stream containing C4 and higher hydrocarbons.

19. The light olefins synthesis process of embodiments 15 through 18 and each of the subsequent embodiments (individually and in combination) wherein at least a portion of the stream containing C4 hydrocarbons separated in step (h) is recycled to be cracked with the first stream containing C4 and higher hydrocarbons.

20. The light olefins synthesis process of embodiments 15 through 19 and each of the subsequent embodiments (individually and in combination) wherein at least a portion of the second stream containing C4 and higher hydrocarbons is cracked with the hydrocarbon stream.

21. The light olefins synthesis process of embodiments 15 through 20 and each of the subsequent embodiments (individually and in combination) wherein the co-fractionation of step (f) comprises separating the first and second cracked gas effluent streams containing light olefins into a first stream containing C5 and lighter hydrocarbons and a pygas stream containing C5 and higher hydrocarbons.

22. The light olefins synthesis process of embodiments 15 through 21 and each of the subsequent embodiments (individually and in combination) wherein at least a portion of the first stream containing C5 and lighter hydrocarbons is treated to separate the second light olefins-containing stream from the second stream containing C4 and higher hydrocarbons.

23. The light olefins synthesis process of embodiments 15 through 22 and each of the subsequent embodiments (individually and in combination) wherein at least a portion of the pygas stream containing C5 and higher hydrocarbons is hydrogenated and then separated into a stream containing C6 and higher hydrocarbons and a stream containing C5 and lighter hydrocarbons 24. The light olefins synthesis process of embodiments 15 through 23 and each of the subsequent embodiments (individually and in combination) wherein at least a portion of the stream containing the C5 and lighter hydrocarbons optionally is selectively hydrogenated and then cracked with the first stream containing C4 and higher hydrocarbons.

25. The light olefins synthesis process of embodiments 15 through 26 (individually and in combination) wherein at least a portion of the pygas stream containing C5 and higher hydrocarbons produced by the co-fractionation of step (f) is subjected to a single step of hydrotreatment without any associated depentanizing.

26. A light olefins synthesis process, including the process of any of the previous embodiments, wherein a stream containing C4 hydrocarbons is optionally selectively hydrogenating and then the optionally selectively hydrogenated stream is fractionated to separate a 2-butene stream from a first 1-butene stream.

27. The light olefins synthesis process of the previous embodiment wherein the 2-butene stream is cracked with the first stream containing C4 and higher hydrocarbons.

28. The light olefins synthesis process of the previous two embodiments wherein isobutylene in the 1-butene stream is reacted with methanol to produce MTBE and the MTBE is recovered separately from a second 1-butene stream.

29. The light olefins synthesis process of the previous three embodiments wherein the second 1-butene stream is fractionated to produce a 1-butene product stream separate from a C4 paraffins stream.

The present invention has been described with reference to specific embodiments. However, this application is intended to cover those changes and substitutions that may be made by those skilled in the art without departing from the spirit and the scope of the invention. Unless otherwise specifically indicated, all percentages are by weight.

The invention claimed is:

1. A light olefins synthesis process comprising:
(a) passing an oxygenate feed to an oxygenate-to-olefin reactor to contact the oxygenate feed with a molecular sieve catalyst and to convert oxygenate feed to light olefins which are discharged from the oxygenate-to-olefin reactor in an effluent stream;
(b) separating the effluent stream into a first light olefins stream separate from a first stream containing C4 and higher hydrocarbons;
(c) selectively hydrogenating and then cracking the first stream containing C4 and higher hydrocarbons to form a first cracked gas effluent stream containing light olefins;
(d) separately cracking a hydrocarbon stream to form a second cracked gas effluent stream containing light olefins;
(e) co-fractionating the first and second cracked gas effluent streams to produce a second light olefins-containing stream separate from a second stream containing C4 and higher hydrocarbons;
(f) co-conditioning the first and second light olefins-containing streams to remove acid gases and produce a conditioned stream; and
(g) separating the conditioned stream into an ethylene product stream, a propylene product stream and a stream containing C4 hydrocarbons and
(h) optionally selectively hydrogenating the stream containing C4 hydrocarbons and then fractionating the optionally selectively hydrogenated stream to separate a 2-butene stream from a first 1-butene stream.

2. The light olefins synthesis process of claim 1 wherein the 2-butene stream is cracked with the first stream containing C4 and higher hydrocarbons.

3. The light olefins synthesis process of claim 2 wherein isobutylene in the 1-butene stream is reacted with methanol to produce MTBE and the MTBE is recovered separately from a second 1-butene stream.

4. The light olefins synthesis process of claim 1 wherein the second 1-butene stream is fractionated to produce a 1-butene product stream separate from a C4 paraffins stream.

5. The light olefins synthesis process of claim 1 wherein the separate cracking of step (d) comprises a stream pyrolysis of one or more of naphtha, liquefied petroleum gas (LPG), propane, ethane, raffinate, gas condensates, atmospheric gas oils and hydrocracker bottoms.

6. The light olefins synthesis process of claim 5 wherein at least a portion of the second stream containing C4 and higher hydrocarbons is cracked with the first stream containing C4 and higher hydrocarbons.

7. The light olefins synthesis process of claim 5 wherein at least a portion of the second stream containing C4 and higher hydrocarbons is selectively hydrogenated and then cracked with the first stream containing C4 and higher hydrocarbons.

8. The light olefins synthesis process of claim 5 wherein at least a portion of the stream containing C4 hydrocarbons separated in step (g) is recycled to be cracked with the first stream containing C4 and higher hydrocarbons.

9. The light olefins synthesis process of claim 5 wherein at least a portion of the second stream containing C4 and higher hydrocarbons is cracked with the hydrocarbon stream.

10. The light olefins synthesis process of claim 1 wherein the separate cracking of the hydrocarbon stream of step (d) forms both the second cracked gas effluent stream containing light olefins and a pyrolysis gas stream containing C4 and higher hydrocarbons.

11. The light olefins synthesis process of claim 10 wherein the pyrolysis gas stream containing C4 and higher hydrocarbons is selectively hydrogenated to produce a third stream containing C4 and higher hydrocarbons, and the third stream containing C4 and higher hydrocarbons is cracked with the first stream containing C4 and higher hydrocarbons.

12. The light olefins synthesis process of claim 10 wherein the pyrolysis gas stream containing C4 and higher hydrocarbons is blended with the first and second cracked gas effluent streams containing light olefins to produce a blended stream prior to the co-fractionation of step (e).

13. The light olefins synthesis process of claim 1 wherein the co-fractionation of step (e) comprises first separating the first and second cracked gas effluent streams containing light olefins into a first stream containing C5 and lighter hydrocarbons and a first stream containing C5 and higher hydrocarbons.

14. The light olefins synthesis process of claim 13 wherein the first stream containing C5 and lighter hydrocarbons is treated to separate the second light olefins-containing stream from the second stream containing C4 and higher hydrocarbons.

15. The light olefins synthesis process of claim 12 wherein co-fractionation of the blended stream of the pyrolysis gas stream containing C4 and higher hydrocarbons and the first and second cracked gas effluent streams containing light olefins produces the first stream containing C5 and lighter hydrocarbons and the first stream containing C5 and higher hydrocarbons.

16. The light olefins synthesis process of claim 13 wherein the first stream containing C5 and higher hydrocarbons is treated to separate a stream containing C6 and higher hydrocarbons from a second stream containing C4 hydrocarbons.

17. The light olefins synthesis process of claim 16 wherein the second stream containing C4 hydrocarbons is selectively hydrogenated and then cracked with the first stream containing C4 and higher hydrocarbons.

18. The light olefins synthesis process of claim 1 wherein the second cracked gas effluent stream containing light olefins formed in step (d) contains C8 and lighter hydrocarbons produced as an overhead of a water quench.

19. The light olefins synthesis process of claim 18 wherein C6 and heavier hydrocarbons are removed from the stream of C8 and lighter hydrocarbons by compression.

20. The light olefins synthesis process of claim 19 wherein a blend of the first cracked gas effluent stream and the second cracked gas effluent stream from which C6 and heavier hydrocarbons have been removed is fractionated to produce a second light olefins-containing stream separate from a second stream containing C4 and higher hydrocarbons.

* * * * *